(12) United States Patent
Svendsen et al.

(10) Patent No.: US 7,279,452 B2
(45) Date of Patent: Oct. 9, 2007

(54) SANITIZING APPLICATOR HAVING A POSITIVELY CHARGED FABRIC COVER

(75) Inventors: Jeffrey S. Svendsen, Plano, TX (US); Steven W. Smith, Dallas, TX (US)

(73) Assignee: Commun-i-tec, Ltd., Dallas, TX (US)

( * ) Notice: Subject to any disclaimer, the term of this patent is extended or adjusted under 35 U.S.C. 154(b) by 298 days.

(21) Appl. No.: 11/151,572

(22) Filed: Jun. 13, 2005

(65) Prior Publication Data

US 2005/0255016 A1 Nov. 17, 2005

Related U.S. Application Data

(63) Continuation-in-part of application No. 10/945,722, filed on Sep. 21, 2004, now Pat. No. 6,916,776, which is a continuation of application No. 10/210,994, filed on Aug. 2, 2002, now Pat. No. 6,794,352, which is a continuation-in-part of application No. 09/591,923, filed on Jun. 12, 2000, now abandoned.

(51) Int. Cl.
*C11D 1/62* (2006.01)

(52) U.S. Cl. ............. 510/438; 510/234; 510/237; 510/238; 510/245; 510/254; 510/363; 510/365; 510/382; 510/384; 510/391; 510/504

(58) Field of Classification Search ........... 501/234, 501/237, 238, 245, 254, 363, 365, 382, 384, 501/391, 438, 504
See application file for complete search history.

(56) References Cited

U.S. PATENT DOCUMENTS

| | | | |
|---|---|---|---|
| 2,702,780 A | 2/1955 | Lerner | |
| 2,982,682 A | 5/1961 | Kine et al. | |
| 4,489,192 A | 12/1984 | Shih et al. | |
| 4,514,461 A * | 4/1985 | Woo | 442/96 |
| 4,654,256 A * | 3/1987 | Doree et al. | 428/304.4 |
| 4,675,437 A | 6/1987 | Knofel et al. | |
| 4,702,947 A | 10/1987 | Pall et al. | |
| 4,737,405 A | 4/1988 | Bouchette | |
| 4,755,421 A | 7/1988 | Manning | |
| 4,791,161 A | 12/1988 | Leising | |
| 4,898,633 A * | 2/1990 | Doree et al. | 156/145 |
| 4,902,503 A | 2/1990 | Umemura et al. | |
| 4,929,498 A | 5/1990 | Suskind et al. | |
| 5,252,663 A | 10/1993 | Chandran et al. | |
| 5,475,903 A | 12/1995 | Collins et al. | |
| 6,139,856 A * | 10/2000 | Kaminska et al. | 424/404 |
| 6,713,156 B1 | 3/2004 | Pauls et al. | |
| 6,716,805 B1 | 4/2004 | Sherry et al. | |
| 6,916,480 B2 | 7/2005 | Anderson et al. | |
| 6,936,580 B2 | 8/2005 | Sherry et al. | |
| 7,160,846 B2 | 1/2007 | Biering et al. | |
| 2003/0008591 A1 | 1/2003 | Parsons et al. | |
| 2003/0032352 A1 | 2/2003 | Chang et al. | |
| 2003/0113364 A1 | 6/2003 | McAtee et al. | |
| 2003/0125224 A1 | 7/2003 | Seitz, Jr. et al. | |
| 2003/0135181 A1 * | 7/2003 | Chen et al. | 604/374 |
| 2003/0176133 A1 | 9/2003 | Walker et al. | |
| 2003/0194932 A1 | 10/2003 | Clark et al. | |
| 2004/0228904 A1 | 11/2004 | Ellis et al. | |
| 2005/0239356 A1 | 10/2005 | Parsons et al. | |
| 2005/0287353 A1 * | 12/2005 | Trogolo | 428/323 |
| 2006/0128242 A1 | 6/2006 | Walker et al. | |
| 2006/0128248 A1 | 6/2006 | Elis | |
| 2006/0166849 A1 | 7/2006 | Kilkenny et al. | |
| 2007/0032151 A1 | 2/2007 | Ellis | |
| 2007/0071537 A1 * | 3/2007 | Reddy et al. | 401/196 |

FOREIGN PATENT DOCUMENTS

| | | |
|---|---|---|
| EP | 0136649 A2 | 4/1985 |
| EP | 0141628 A1 | 5/1985 |
| EP | 0118327 B1 | 4/1987 |
| EP | 0318258 A2 | 5/1989 |
| EP | 1065302 A1 | 1/2001 |
| EP | 1661586 A1 | 5/2006 |
| JP | 62-263211 | 11/1987 |
| WO | WO 02/077048 A2 | 10/2002 |
| WO | WO 03/048441 A1 | 6/2003 |
| WO | WO 04/000373 A1 | 12/2003 |
| WO | WO 2004/064876 A2 | 8/2004 |
| WO | WO 2007/016579 | 2/2007 |

* cited by examiner

*Primary Examiner*—Charles Boyer
(74) *Attorney, Agent, or Firm*—Steven W. Smith

(57) ABSTRACT

A sanitizing applicator for applying a liquid sanitizer to a surface. The sanitizer may be a quaternary ammonium compound (QAC)-based or chlorine-based sanitizer containing positively charged ions at an effective concentration level for killing a predefined percentage of microbes present on the surface. The applicator includes a breakable internal reservoir for retaining a quantity of the sanitizer, and a positively charged nonwoven fabric covering the reservoir. The fabric is constructed using a positively charged binder to bind together the strands of the fabric, and is optionally treated with a positively or neutrally charged surfactant. The positive charge of the fabric prevents the fabric from neutralizing the positively charged ions in the sanitizer when the breakable internal reservoir is broken and the sanitizer is applied to the fabric.

19 Claims, 2 Drawing Sheets

SANITIZING APPLICATOR HAVING A POSITIVELY CHARGED FABRIC COVER

RELATED APPLICATIONS

This application is a continuation-in-part of U.S. patent application Ser. No. 10/945,722 entitled, *Article for Sanitizing a Surface Comprising a Wipe Containing an Adhesive, Positively Charged, Binder*, filed Sep. 21, 2004 now U.S. Pat. No. 6,916,776 in the name of Jeffrey S. Svendsen; which is a continuation of U.S. patent application Ser. No. 10/210,994 entitled, *Sanitizing Towel Having a Color Identifying Label and Sanitizer Release Polymer Composition*, filed Aug. 2, 2002 now U.S. Pat. No. 6,794,352 in the name of Jeffrey S. Svendsen, now U.S. Pat. No. 6,794,352; which is a continuation-in-part of U.S. patent application Ser. No. 09/591,923 entitled, *Method of Ensuring Proper Utilization of Specialized Tools*, filed Jun. 12, 2000 now abandoned in the name of Jeffrey S. Svendsen, now abandoned; all of the disclosures of which are fully incorporated herein by reference.

BACKGROUND OF THE INVENTION

1. Technical Field of the Invention

This invention relates to sanitizing and sanitizing supplies. More particularly, and not by way of limitation, the present invention is directed to a sanitizing applicator having an internal sanitizer reservoir and a positively charged fabric cover.

2. Description of Related Art

A problem encountered in restaurants is the control of microbial growth on surfaces such as tables, kitchen counters, and bathroom fixtures. To control microbial growth on a surface, a sanitizing solution containing antimicrobials such as sanitizers is applied to the surface with a woven or nonwoven fabric. In the restaurant industry, government Public Health requirements dictate that sanitizing solutions must reduce microbial contaminants to a safe level. Currently, the safe level is a 99.999% reduction in the bacterial count.

The same problem occurs in homes and in health care facilities such as hospitals, clinics, and doctors' offices where it is equally or more important to control microbial growth.

For the sanitization process to be effective, the sanitizing solution must maintain a certain concentration of sanitizer. A serious problem occurs when fabric of the sanitizing towel dilutes the concentration of sanitizer in the sanitizing solution. For example, a nonwoven fabric is repeatedly rinsed in a sanitizing solution contained in a bucket, while sanitizing the tabletop surfaces of a restaurant. If the nonwoven fabric is diluting the sanitizer in the sanitizing solution, then the tabletop surfaces are not being disinfected. This can lead to an outbreak of pathogenic enteric bacteria, such as nearly all members of the genus *Salmonella* or *E. coli*. Pathogenic enteric bacteria can cause illness, or worse death.

The two most common sanitizers in sanitizing solutions are quaternary ammonium compound (QAC)-based or chlorine-based sanitizers. A QAC is an ion, which is a molecule that carries an electric charge. More specifically, a QAC is a cation, that is an ion that posses a positive charge. A nonionic molecule is an ion that posses a neutral charge. An anion is an ion that posses a negative charge. The charge of a molecule affects that molecule's intermolecular interactions. For example, a cation is attracted to an anion, and a cation repels another cation.

Nonwoven fabrics in common use today with sanitizing solutions are made with anionic (i.e., negatively charged) binders and surfactants. The negative charge of the anionic binders and surfactants utilized in nonwoven fabrics attracts and bonds the cationic QAC-based sanitizer to the fabric thereby diluting and neutralizing the concentration of sanitizer in the sanitizing solution. Moreover, woven fabrics comprise many interwoven strands of material, thereby creating a large irregular surface area that captures a large number of cationic QACs during use, thereby diluting the concentration of sanitizer in the sanitizing solution. Existing methods to solve this problem are to regularly replace the sanitizing solution or regularly replenish the concentration of sanitizer. However, these existing methods are not without limitations.

These existing methods are time consuming and expensive. Regularly monitoring and replacing or replenishing the sanitizing solution involves considerable employee time and the expense associated with replacing or replenishing the sanitizing solution. Additionally, during busy times in many restaurants and hospitals, replacement or replenishment of the sanitizing solution is often forgotten, resulting in insufficient levels of microbial reduction.

It is also noted that nonwoven fabrics manufactured with a high pulp content are initially sanitizer-friendly; that is, at first, they have little effect on the concentration level of the sanitizer. However, the pulp content makes them less durable and subject to shredding when they become wet. Additionally, once such fabrics have been rinsed, they lose their sanitizer-friendly properties and begin to adversely affect the sanitizer concentration level.

Therefore, a need has arisen for a sanitizing applicator that overcomes the disadvantages of the existing art. The present invention provides such a sanitizing applicator.

SUMMARY OF THE INVENTION

In one aspect, the present invention is directed to a sanitizing applicator for applying a liquid sanitizer to a surface. The sanitizer comprises positively charged ions at an effective concentration level for killing a predefined percentage of microbes present on the surface. The applicator includes a breakable internal reservoir for retaining a quantity of the sanitizer; and a positively charged fabric covering the breakable internal reservoir. The positive charge of the fabric prevents the fabric from neutralizing the positively charged ions in the sanitizer when the breakable internal reservoir is broken and the sanitizer is applied to the fabric.

In another aspect, the present invention is directed to a method of manufacturing a sanitizing applicator, which is utilized to apply a liquid sanitizer to a surface. The method includes filling a breakable internal reservoir with a quantity of the sanitizer; constructing a positively charged nonwoven fabric; and covering the breakable internal reservoir with the positively charged nonwoven fabric.

In yet another aspect, the present invention is directed to a combination for sanitizing a surface. The combination includes a liquid sanitizer comprising positively charged ions at an effective concentration level for killing a predefined percentage of microbes present on the surface, and a sanitizing applicator. The sanitizing applicator includes a breakable internal reservoir for retaining a quantity of the sanitizer, and a positively charged fabric covering the breakable internal reservoir. The positive charge of the fabric prevents the fabric from neutralizing the positively charged ions in the sanitizer when the breakable internal reservoir is broken and the sanitizer is applied to the fabric.

BRIEF DESCRIPTION OF THE DRAWINGS

The invention will be better understood and its numerous objects and advantages will become more apparent to those skilled in the art by reference to the following drawings, in conjunction with the accompanying specification, in which.

DETAILED DESCRIPTION OF EMBODIMENTS

Figure 1:
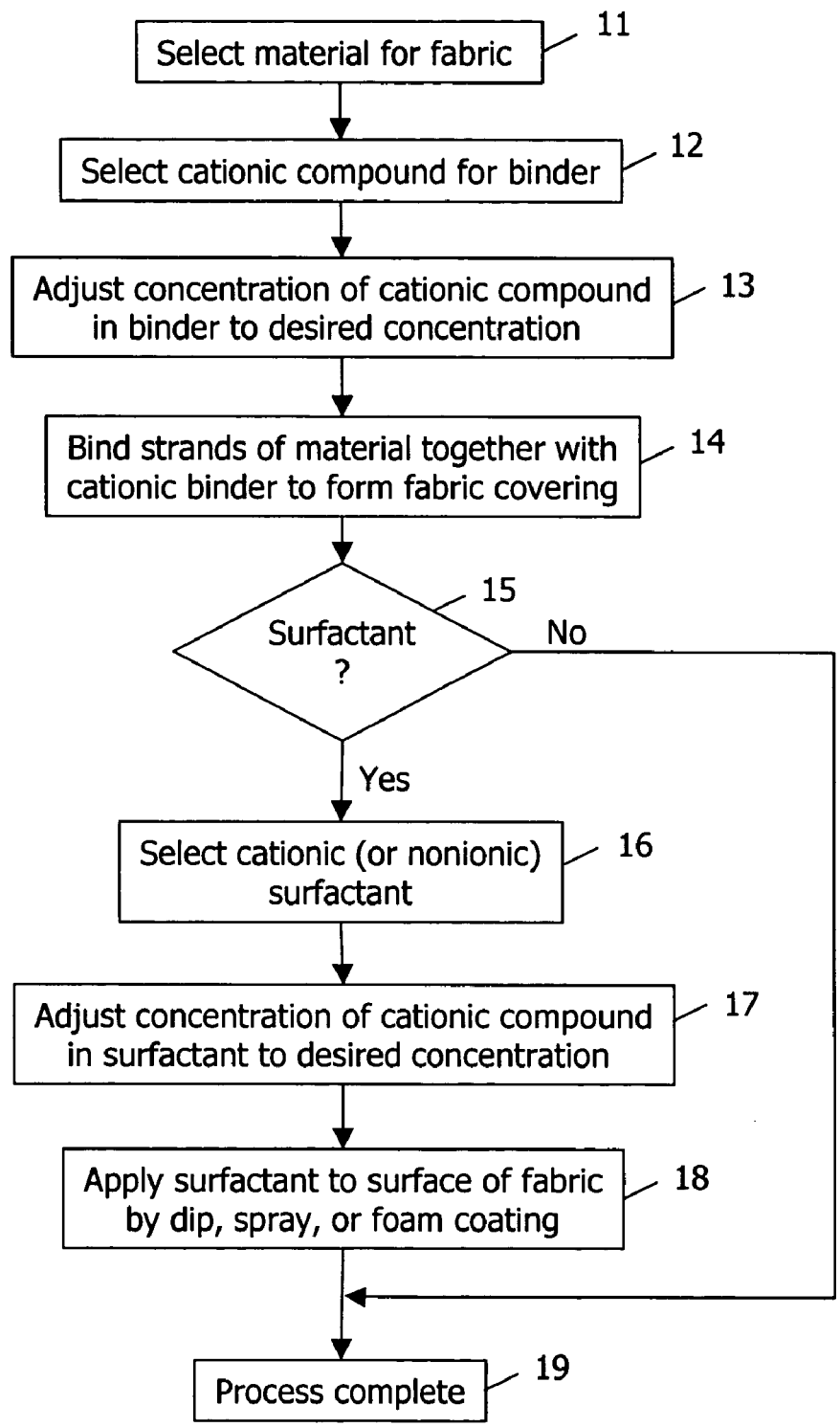
FIG. 1 is a flow chart outlining the steps of a process for manufacturing the positively charged fabric for a sanitizing applicator in a preferred embodiment of the present invention.

The present invention provides a sanitizing applicator having an internal sanitizer reservoir and a positively charged fabric cover. The fabric cover is preferably a non-woven material manufactured with an adhesive, positively charged binder. The fabric may also be treated with at least one cationic surfactant, which is embedded into the strands of the fabric during manufacturing. Additionally, the fabric may be treated with at least one co-surfactant. Optionally, the surfactant and/or co-surfactant(s) may contain one or more additive agents that functionally and chemically improve the bonding of the cationic surfactant and co-surfactant(s) to a particular fabric. In an alternative embodiment, the surfactants are nonionic surfactants.

The purpose of any finish, such as a surfactant, is to improve the aesthetic, functional or processing properties of fabrics. Surfactants are a class of materials broadly characterized as being made of molecules containing hydrophilic groups adequately separated from hydrophobic groups. The hydrophobic groups have an affinity for the fiber surface. The hydrophilic groups are attached predominantly to the aqueous medium. Existing fabrics used in the field of sanitizers use anionic surfactants that attract the cationic QAC-based and cationic chlorine-based sanitizers thereby diluting the concentration of sanitizer in the sanitizing solution. The fabric of the present invention achieves its unexpectedly superior sanitizer properties by preferably utilizing a cationic binder that repels the cationic QAC-based and cationic chlorine-based sanitizers thereby not diluting the concentration of sanitizer in the sanitizing solution. In other embodiments, the fabric is treated with cationic or nonionic surfactants.

Suitable cationic surfactants include, for example:
dieicosyldimethyl ammonium chloride;
didocosyldimethyl ammonium chloride;
dioctadecyidimethyl ammonium chloride;
dioctadecyldimethyl ammonium methosulphate;
ditetradecyldimethyl ammonium chloride and naturally occurring mixtures of above fatty groups, e.g. di(hydrogenated tallow)dimethyl ammonium chloride;
di(hydrogenated tallow)dimethyl ammonium metho-sulphate;
ditallow dimethyl ammonium chloride; and
dioleyidimethyl ammonium chloride.

Suitable cationic surfactants also include imidazolinium compounds, for example, 1-methyl-1-(tallowylamido-)ethyl-2-tallowyl4,5-dihydroimidazolinium methosulphate and 1-methyl-1-(palmitoylamido)ethyl-2-octadecyl 4,5-dihydro-imidazolinium methosulphate. Other useful imidazolinium materials are 2-heptadecyl-1-methyl-1(2-stearoylamido)-ethyl-imidazolinium methosulphate and 2-lauryl-lhydroxyethyl-1-oleyl-imidazolinium chloride.

Further examples of suitable cationic surfactants include:
dialkyl($C_{12}$-$C_{22}$)dimethylammonium chloride;
alkyl(coconut)dimethylbenzylammonium chloride;
octadecylamine acetate salt;
tetradecylamine acetate salt;
tallow alkylpropylenediamine acetate salt;
octadecyltrimethylammonium chloride;
alkyl(tallow)trimethylammonium chloride;
dodecyltrimethylammonium chlorid;
alkyl(coconut)trimethylammonium chloride;
hexadecyltrimethylammonium chloride;
biphenyltrimethylammonium chloride, alkyl(tallow)-imidazoline quaternary salt;
tetradecylmethylbenzylammonium chloride;
octadecyidimethylbenzylammonium chloride;
dioleyidimethylammonium chloride;
polyoxyethylene dodecylmonomethylammonium chloride;
polyoxyethylene alkyl($C_{12}$-$C_{22}$)benzylammonium chloride;
polyoxyethylene laurylmonomethyl ammonium chloride;
1-hydroxyethyl-2-alkyl(tallow)-imidazoline quaternary salt; and
a silicone cationic surfactant having a siloxane group as a hydrophobic group, a fluorine-containing cationic surfactant having a fluoroalkyl group as a hydrophobic group.

Suitable nonionic surfactants include, for example, from $C_6$ to $C_{12}$ alkylphenol ethoxylates, from $C_8$ to $C_{20}$ alkanol alkoxylates, and block copolymers of ethylene oxide and propylene oxide. Optionally, the end groups of polyalkylene oxides can be blocked, whereby the free OH groups of the polyalkylene oxides can be etherified, esterified, acetalized and/or aminated. Another modification consists of reacting the free OH groups of the polyalkylene oxides with isocyanates. The nonionic surfactants also include $C_4$ to $C_{18}$ alkyl glucosides as well as the alkoxylated products obtainable therefrom by alkoxylation, particularly those obtainable by reaction of alkyl glucosides with ethylene oxide.

Suitable amphoteric surfactants contain both acidic and basic hydrophilic groups. Amphoteric surfactants are preferably derivatives of secondary and tertiary amines, derivatives of quaternary ammonium, quaternary phosphonium or tertiary sulfonium compounds. The cationic atom in the quaternary compound can be part of a heterocyclic ring. The amphoteric surfactant preferably contains at least one aliphatic group, containing about 3 to about 18 carbon atoms.

As noted above, the fabric may optionally be treated with a co-surfactant. Suitable co-surfactants are selected from nonionic, anionic, amphoteric, zwitterionic and semi-polar surfactants. A combination of cationic surfactants and cationic co-surfactants may also be utilized.

At least one cationic compound is present in the binder in an amount of from about 0.1 to about 99 weight percent, preferably from 0.5 to 50 weight percent, more preferably from 1 to 10 weight percent, based on the total weight of the binder. Preferable binders and surfactants can be obtained from Chicopee, Inc. of Dayton, N.J., a part of Polymer Group Inc. (PGI).

The composition of the additive agents, such as, for example, crosslinking or curing agents, that functionally and chemically improve the bonding of the cationic surfactant and optional co-surfactant to a particular fabric will depend on the composition and rheology of the fabric.

FIG. 1 is a flow chart outlining the steps of a process for manufacturing a fabric for the cover of the sanitizing applicator in a preferred embodiment of the present invention. At step 11, a suitable material is selected for the fabric, depending on the desired texture and strength of the cover. At step 12, a cationic compound is selected for the binder. At step 13, the concentration of the cationic compound in the binder is adjusted, depending on the adhesive properties of the binder and the desired level of positive charge desired for the fabric. At step 14, the strands of the material are bound together with the cationic binder to form the fabric cover.

At step 15, it is determined whether or not a surfactant is also to be utilized on the fabric. If not, the process moves to step 19. If a surfactant is to be utilized, the process moves to step 16 where a suitable cationic (or nonionic) surfactant is selected. At step 17, the concentration of the cationic surfactant is preferably adjusted to a range of 1 to 10 weight percent, based on the total weight of the surfactant. At step 18, the surfactant is applied to the surface of the fabric. It should be understood by one skilled in the art that the bonding of the surfactant to the fabric will depend on the composition and rheology of the fabric. The surfactant may be applied to the surface of the fabric by any suitable method. For example, the surfactant may be diluted with an organic solvent or water, and then applied to the surface of the fabric by dip coating, spray coating, or foam coating. The process is then complete at step 19.

Figure 2:
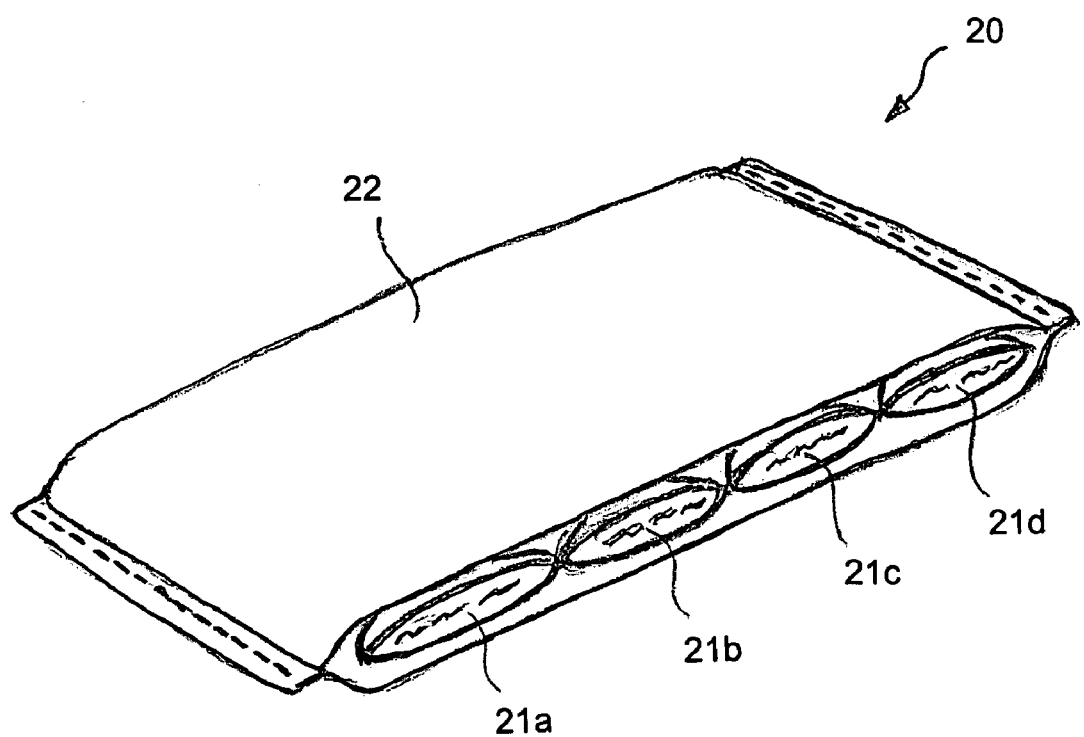
FIG. 2 is a perspective view of a sanitizing applicator with a cut-away section to reveal the sanitizer reservoirs contained therein.

FIG. 2 is a perspective view of a sanitizing applicator 20 with a cut-away section to reveal a plurality of sanitizer reservoirs 21a-21d contained therein. The sanitizing applicator is covered by the positively charged fabric 22. In the exemplary embodiment shown, the sanitizer reservoirs are similar in construction to the well-known packaging material known as "bubble wrap". However, instead of being filled with air, the "bubbles" are preferably filled with a liquid QAC-based or chlorine-based sanitizer. When a user desires to sanitize a surface, the user squeezes the applicator, causing the sanitizer reservoirs to burst and release the sanitizer. The sanitizer reservoirs have a tensile strength such that the bubble will burst and release the sanitizer when the user squeezes the applicator with a predefined amount of force. The predefined amount of force is selected in a range in which users will not accidentally break the reservoirs, but it does not require so much force that users have difficulty breaking the reservoirs. In one embodiment, the sanitizer reservoirs have a tensile strength that will withstand a force of approximately 20 pounds per square inch before breaking.

Once the sanitizer reservoirs 21a-21d are broken, the sanitizer is absorbed by the fabric cover 22, and the applicator can then be used to apply the sanitizer to the desired surface. Because the fabric cover is positively charged, the concentration level of the sanitizer is not reduced prior to application to the desired surface.

It should be recognized that other configurations of the sanitizer reservoirs 21 are possible, such as a single reservoir "bubble", longitudinal channels, lateral channels, and the like. The invention is not limited to the specific exemplary configuration shown. It may also be desirable in some embodiments of the invention, to manufacture the reservoir bubbles within a thicker and stiffer lattice-type framework. Such a framework gives the entire applicator more stiffness, providing for easier handling when applying the sanitizer to the desired surface.

It is thus believed that the operation of the present invention will be apparent from the foregoing description. While the sanitizing applicator shown and described has been characterized as being preferred, it will be readily apparent that various changes and modifications could be made therein without departing from the scope of the invention as defined in the following claims.

What is claimed is:

1. A sanitizing applicator for applying a liquid sanitizer to a surface, said sanitizer comprising positively charged ions at an effective concentration level for killing a predefined percentage of microbes present on the surface, said applicator comprising:

a breakable internal reservoir for retaining a quantity of the sanitizer; and a positively charged fabric covering the breakable internal reservoir, said positively charged fabric including an adhesive binder that binds together a multiplicity of strands to form the fabric, said binder including positively charged ions that provide the fabric with a predominantly positive charge;

wherein the positive charge of the fabric prevents the fabric from neutralizing the positively charged ions in the sanitizer when the breakable internal reservoir is broken and the sanitizer is applied to the fabric.

2. The sanitizing applicator of claim 1, wherein the positively charged fabric is also treated during manufacturing with a positively charged surfactant that is embedded into the strands of the fabric.

3. The sanitizing applicator of claim 1, wherein the positively charged fabric is also treated during manufacturing with a neutrally charged surfactant that is embedded into the strands of the fabric.

4. The sanitizing applicator of claim 1, wherein the breakable internal reservoir includes at least one plastic bubble filled with the liquid sanitizer, said plastic bubble having a tensile strength such that the bubble will burst and release the sanitizer when a user squeezes the applicator with a predefined amount of force.

5. The sanitizing applicator of claim 1, wherein the breakable internal reservoir includes a plurality of adjoining plastic bubbles filled with liquid sanitizer, each of the plastic bubbles having a tensile strength such that the bubbles will burst and release the sanitizer when a user squeezes the applicator with a predefined amount of force.

6. The sanitizing applicator of claim 5, wherein the applicator is rectangular in shape, and the breakable internal reservoir includes a plurality of elongate reservoirs oriented so that the reservoirs are parallel to a longitudinal axis of the applicator.

7. The sanitizing applicator of claim 5, wherein the applicator is rectangular in shape, and the breakable internal reservoir includes a plurality of elongate reservoirs oriented so that the reservoirs are perpendicular to a longitudinal axis of the applicator.

8. The sanitizing applicator of claim 5, wherein the breakable internal reservoir also includes a stiff lattice-type framework in which the plurality of plastic bubbles are mounted.

9. A method of manufacturing a sanitizing applicator, said sanitizing applicator being utilized to apply a liquid sanitizer to a surface, said sanitizer comprising positively charged ions at an effective concentration level for killing a predefined percentage of microbes present on the surface, said method comprising:

filling a breakable internal reservoir with a quantity of the sanitizer;

constructing a positively charged nonwoven fabric, said constructing step including:

selecting an adhesive binder comprising predominantly positively charged ions; and applying the binder to a plurality of loose strands of material to bind the strands together into a web-like structure forming the fabric; and covering the breakable internal reservoir with the positively charged nonwoven fabric.

10. The method of claim 9, further comprising the step of selecting a suitable liquid sanitizer comprising positively charged ions at or above the effective concentration level for killing the predefined percentage of microbes present on the surface.

11. The method of claim 9, further comprising the step of:

constructing a plurality of adjoining plastic bubbles for retaining the liquid sanitizer, each of the plastic bubbles having a tensile strength such that the bubbles will burst and release the sanitizer when a user squeezes the applicator with a predefined amount of force.

12. The method of claim 11, wherein the step of constructing a plurality of adjoining plastic bubbles includes mounting the plurality of plastic bubbles in a stiff lattice-type framework.

13. A combination for sanitizing a surface, said combination comprising:

a liquid sanitizer comprising positively charged ions at an effective concentration level for killing a predefined percentage of microbes present on the surface; and a sanitizing applicator comprising:

a breakable internal reservoir for retaining a quantity of the sanitizer; and a positively charged fabric covering the breakable internal reservoir, wherein the positively charged fabric includes an adhesive binder that binds together a multiplicity of strands to form the fabric, said binder including compounds with positively charged ions that provide the fabric with a predominantly positive charge;

wherein the positive charge of the fabric prevents the fabric from neutralizing the positively charged ions in the sanitizer when the breakable internal reservoir is broken and the sanitizer is applied to the fabric.

14. The combination of claim 13, wherein the positively charged fabric is also treated during manufacturing with a positively charged surfactant that is embedded into the strands of the fabric.

15. The combination of claim 13, wherein the positively charged fabric is also treated during manufacturing with a neutrally charged surfactant that is embedded into the strands of the fabric.

16. The combination of claim 13, wherein the breakable internal reservoir includes at least one plastic bubble filled with the liquid sanitizer, said plastic bubble having a tensile strength such that the bubble will burst and release the sanitizer when a user squeezes the applicator with a predefined amount of force.

17. The sanitizing applicator of claim 1, wherein the positive charge of the fabric substantially prevents the fabric from neutralizing the positively charged ions in the sanitizer when the breakable internal reservoir is broken and the sanitizer is applied to the fabric.

18. The sanitizing applicator of claim 1, wherein the positive charge of the fabric completely prevents the fabric from neutralizing the positively charged ions in the sanitizer when the breakable internal reservoir is broken and the sanitizer is applied to the fabric.

19. The sanitizing applicator of claim 1, wherein the positive charge of the fabric prevents the fabric from neutralizing most of the positively charged ions in the sanitizer when the breakable internal reservoir is broken and the sanitizer is applied to the fabric.

* * * * *